United States Patent [19]

Devore et al.

[11] Patent Number: 5,625,087

[45] Date of Patent: Apr. 29, 1997

US005625087A

[54] SILYLIUM CATIONIC POLYMERIZATION ACTIVATORS FOR METALLOCENE COMPLEXES

[75] Inventors: David D. Devore; David R. Neithamer; Robert E. LaPointe; Robert D. Mussell, all of Midland, Mich.

[73] Assignee: The Dow Chemical Company, Midland, Mich.

[21] Appl. No.: 304,314

[22] Filed: Sep. 12, 1994

[51] Int. Cl.$^6$ .............................. C07F 7/04; C07F 7/08; C07F 7/02

[52] U.S. Cl. .............. 556/468; 502/158; 526/126; 556/173; 556/402; 556/413

[58] Field of Search ........................ 502/151, 152, 502/155, 158; 556/170, 413, 173, 402, 468

[56] References Cited

U.S. PATENT DOCUMENTS

| | | | |
|---|---|---|---|
| 5,064,802 | 11/1991 | Stevens et al. | 502/155 |
| 5,272,236 | 12/1993 | Lai et al. | 526/170 |
| 5,369,196 | 11/1994 | Matsumoto et al. | 526/160 |
| 5,384,299 | 1/1995 | Turner et al. | 502/155 |
| 5,461,128 | 10/1995 | Takeuchi et al. | 526/126 |
| 5,470,993 | 11/1995 | Devore et al | 526/160 |

FOREIGN PATENT DOCUMENTS

| | | |
|---|---|---|
| 416815 | 3/1991 | European Pat. Off. . |
| 93-23412 | 11/1993 | WIPO . |
| WO9323412 | 11/1993 | WIPO . |

OTHER PUBLICATIONS

S. R. Bahr, et al., *J. Am. Chem. Soc.*, 115, 4514–4519 (1993).
M. Kira, et al., *J. Am. Chem. Soc.*, 114, 6697–6700 (1992).
Lambert, J.B., et al., *Organometallics*, 1994, 13,2430–2443.

*Primary Examiner*—Edward J. Smith

[57] ABSTRACT

Catalyst systems useful in addition polymerization reactions comprising a Group 4 metal complex and a silylium salt activating cocatalyst are prepared by contacting the metal complex with a silylium salt of a compatible, non-coordinating anion, optionally the silylium salt is prepared by electrochemical oxidation and splitting of the corresponding disilane compound.

3 Claims, No Drawings

SILYLIUM CATIONIC POLYMERIZATION ACTIVATORS FOR METALLOCENE COMPLEXES

BACKGROUND OF THE INVENTION

This invention relates to a method for preparing compositions of matter that are useful as catalysts, and to a method of using these catalysts for polymerizing addition polymerizable monomers. More particularly the present invention relates to an improved method for preparing a class of catalysts known as cationic metallocene catalysts using a silylium salt activator.

In U.S. Ser. No. 545,403, filed Jul. 3, 1990, (published in equivalent form Mar. 13, 1991 as EP-A-416,815) there are disclosed certain constrained geometry metal complexes and catalysts derived by reacting the metal complex with activating cocatalysts. In U.S. Pat. No. 5,064,802 (published Mar. 20, 1991 in equivalent form as EP-A-418,044) there are further disclosed certain constrained geometry metal catalysts formed by reacting such metal complexes with salts of Bronsted acids containing a non-coordinating compatible anion. The reference discloses the fact that such complexes are usefully employed as catalysts in addition polymerizations. In U.S. Ser. No. 884,966, filed Mar. 15, 1992, U.S. Pat. No. 5,350,723, an alternative technique for preparing cationic constrained geometry catalysts using carbenium cationic activator compounds is disclosed. For the teachings contained therein, the foregoing United States patent and applications are herein incorporated by reference.

It has been previously known in the art to employ carbenium, oxonium or sulfonium ions to generate cationic Group 4 metallocene catalysts. Such a process is disclosed in EP-A2-426,637 published May 8, 1991.

J. B. Lambert, et al., *Organometallics*, 13, 2430–2443 (1994), disclosed a process for preparing silylium borate salts by reaction of carbenium borates with silanes. Lewis base adducts of silylium borates, especially ether and acetonitrile adducts of silylium borates, are disclosed in S. R. Bahr, et al., *J. Am. Chem. Soc.*, 115, 4514–4519 (1993) and in M. Kira, et al., *J. Am. Chem. Soc.*, 114, 6697–6700 (1992), respectively. None of the foregoing references discloses a utility for such silylium compounds in the formation of polymerization catalysts.

It would be desirable if there were provided an improved method that would allow the production of even more efficient catalysts as well as an improved addition polymerization process utilizing such catalysts.

SUMMARY OF THE INVENTION

As a result of investigations carried out by the present inventors there is now discovered a new and improved method for the preparation of catalysts and an improved method for polymerization of addition polymerizable monomers.

In accordance with the present invention there is provided a catalyst system useful for polymerization of addition polymerizable monomers, said system comprising:

A) a metal complex corresponding to the formula:

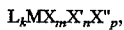

or a dimer thereof wherein:

L is an anionic, delocalized, n-bonded group that is bound to M, containing up to 50 non-hydrogen atoms, optionally two L groups may be joined together forming a bridged structure, and further optionally on L may be bound to X;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X groups may be covalently bound together forming a divalent dianionic moiety having both valences bound to M, or form a neutral, conjugated or nonconjugated diene that is n-bonded to M (whereupon M is in the +2 oxidation state), or further optionally one or more X and one or more X' groups may be bonded together thereby forming a moiety that is both covalently bound to M and coordinated thereto by means of Lewis base functionality;

k is 1 or 2;

m is 0 or 1;

n is a number from 0 to 3;

p is an integer from 0 to 3; and the sum, k+m+p, is equal to the formal oxidation state of M, and B) a silylium salt corresponding to the formula:

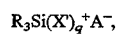

wherein R independently each occurrence is selected from the group consisting of hydrocarbyl, silyl, hydrocarbyloxy, dihydrocarbylamino, and combinations thereof having up to 30 nonhydrogen atoms, X' is as previously defined, q is zero or one, and A⁻ is a noncoordinating, compatible anion.

Also included within the present invention is a process for forming a catalyst system comprising contacting the foregoing components A) and B) in an inert diluent, optionally in the presence of one or more addition polymerizable monomers.

Certain of the above described catalyst systems, especially those in which the metal M is initially in the +4 formal oxidation state, are believed to exist in the form of the corresponding cationic metal complex having the formula:

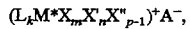

or a dimer thereof wherein:

M* is a metal of Group 4 of the Periodic Table of the Elements in the +4 formal oxidation state;

L, X, X', X", A⁻, k, m, n and p are as previously defined.

Moreover, according to the present invention there is included a novel method of forming the silylium salts or optionally the catalyst system, comprising electrolyzing a solution comprising a disilane compound corresponding to the formula:

wherein R is as previously defined, in the presence of a source of the noncoordinating counter ion, A⁻. To form the catalyst system of the invention, the resulting silylium salt is contacted with the metal complex, $L_kMX_mX'_nX''_p$, or a dimer thereof.

Finally, according to the present invention there is provided a polymerization process comprising contacting one or more addition polymerizable monomers under addition polymerization conditions with a catalyst system as previously defined or a catalyst system prepared according to the previously disclosed process.

Addition polymerization products formed according to the present invented process are oligomeric or polymeric materials usefully employed for use as additives in petroleum products and in the formation of moldings, extrusions, adhesives, impact modifiers for thermoplastic resins and in other uses.

The catalysts systems formed according to the present invention are very stable towards thermal and photochemical decomposition and accordingly are highly effective polymerization initiators.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The term "silylium ion" refers to cationic species that possess an electron deficient tricoordinate silicon atom. Stable silylium ions are such cationic species that are able to exist in solution without decomposition for a time period sufficient to undergo the reactions desired of the present invention. Preferred silylium ions are those ions that are incapable of coordination with the metal atom or only weakly coordinate thereto. Further preferably such ions are capable of abstracting an X" group from the metal complex. The silylium ion may also exist in the form of an adduct with a neutral Lewis base, for example as an ether adduct. Examples of suitable silylium ions for use herein include trimethylsilylium, triethylsilylium, triisopropylsilylium, triisobutylsilylium, trihexylsilylium, methyldiphenylsilylium, methyldiisopropylsilylium, dimethyldodecylsilylium, dimethyloctadecylsilylium, tris(trimethylsilyl)silylium, and ether adducts thereof.

As used herein, the recitation "noncoordinating, compatible anion" means an anion which either does not coordinate to the metal containing portion of the complex (or with respect to the electrochemical formation of the silylium cation explained hereinafter, to the silylium complex) or which is only weakly coordinated thereto thereby remaining sufficiently labile to be displaced by a neutral Lewis base, such as an olefin compound. A noncoordinating, compatible anion specifically refers to a compatible anion which, within the time frame of the desired end use, when functioning as a charge balancing anion in the catalyst system of this invention does not transfer an anionic substituent or fragment thereof to the Group 4 metal complex portion thereby forming neutral byproducts. "Compatible anions" are also anions that are not degraded to neutrality when the initially formed complex decomposes and that are noninterfering with the desired subsequent polymerization or other uses of the complex.

More particularly, the noncoordinating, compatible anion may comprise a single coordination complex comprising a charge-bearing metal or metalloid core, which anion is both bulky and non-nucleophilic. The recitation "metalloid", as used herein, includes non-metals such as boron, phosphorus and the like which exhibit semi-metallic characteristics.

Preferred compatible noncoordinating anions, $A^-$, are those containing a single coordination complex comprising a charge-bearing metal or metalloid core, which anion is capable of stabilizing the catalyst system and sufficiently labile to be displaced by olefinic, diolefinic and acetylenically unsaturated substances or other neutral Lewis bases such as ethers, nitriles and the like. Suitable metals include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

Most preferred compatible non-coordinating anions are tetrakis(pentafluorophenyl)borate, tetrakis(2, 3,5,6-tetrafluorophenyl)borate, tetrakis(2,3,4,5-tetrafluorophenyl)borate, tetrakis(3,4,5-trifluorophenyl)borate, tetrakis(1,2,2-trifluoroethenyl)borate, methyltris(perfluorophenyl)borate and phenyltris(perfluorophenyl)borate.

Examples of silylium complexes usefully employed according to the present invention include:
trimethylsilylium tetrakispentafluorophenylborate,
triethylsilylium tetrakispentafluorophenylborate,
triphenylsilylium tetrakispentafluorophenylborate,
tribenzylsilylium tetrakispentafluorophenylborate,
trimethylsilylium methyltrispentafluorophenylborate,
trimethylsilylium benzyltrispentafluorophenylborate,
triethylsilylium phenyltrispentafluorophenylborate,
triethylsilylium methyltrispentafluorophenylborate,
triphenylsilylium methyltrispentafluorophenylborate,
tribenzylsilylium benzyltrispentafluorophenylborate,
tribenzylsilylium methyltrispentafluorophenylborate,
trimethylsilylium tetrakis(2,3,5,6-tetrafluorophenyl)borate,
triphenylsilylium tetrakis(2,3,5,6-tetrafluorophenyl)borate,
trimethylsilylium tetrakis(3,4,5-trifluorophenyl)borate,
tribenzylsilylium tetrakis(3,4,5-trifluorophenyl)aluminate,
triphenylsilylium methyltris(3,4,5-trifluorophenyl)aluminate,
triethylsilylium tetrakis(1,2,2-trifluoroethenyl)borate,
tricyclohexylsilylium tetrakis(2,3,4,5-tetrafluorophenyl)borate,
dimethyloctadecylsilylium tetrakis(pentafluorophenyl)borate,
tris(trimethylsilyl)silylium methyltris(2,3,4,5tetrafluorophenyl)borate, or an ether adduct thereof.

Such silylium compounds, or their ether adducts, are readily formed by reaction of a silane chloride of the formula $R_3SiCl$, wherein R is as previously defined, with a Group 1 or Group 2 metal salt of the desired noncoordinating, compatible anion, especially lithium tetrakispentafluorophenylborate. Alternatively, the corresponding silane, $R_3SiH$ may be contacted with a carbenium salt of the desired noncoordinating, compatible anion, for example triphenylcarbenium tetrakispentafluorophenylborate. The above reactions are desirably conducted in an inert liquid such as an aromatic or aliphatic hydrocarbon or aliphatic ether. In the latter event the resulting product is generally recovered in the form of an ether adduct. The reaction may also be conducted in situ in the reactor used for addition polymerization or equipment associated therewith and the resulting product utilized as the polymerization catalyst without recovery.

In a further, and highly preferred alternative preparation, the previously identified disilane compound, $R_3SiSiR_3$, is oxidized under inert oxidizing conditions and converted into two cationic products. The term "inert oxidizing conditions" as used herein refers to the use of solvents, oxidizing agents and oxidizing conditions such that byproducts that would render inactive the catalyst system of the present invention are not formed during the reaction. More particularly, suitable solvents are materials that are: liquids under the conditions of the oxidation (generally temperatures from 0° to 100° C.), capable of dissolving the reactants and inert. "Inert solvents" are those that are not reduced or oxidized under the reaction conditions employed. Examples of preferred solvents include difluorobenzene (all isomers), and $C_{1-6}$ dialkyl ethers of (poly)alkylene glycols, especially dimethoxyethane, and mixtures of the foregoing. Generally, solvents that are Lewis bases, especially nitrile, ether, amine, and phosphine compounds may be used.

A preferred process involves the electrolytic oxidation of the disilane compound. General techniques and equipment for electrolysis that are previously well known in the art are used. A disilane that oxidizes at a potential higher than that of the metal complex is employed. A preferred oxidizing potential for such disilane is at least +0.50 volts versus a saturated calomel electrode, more preferably at least +1.50 volts versus a saturated calomel electrode. Cell potentials can be calculated using a known potential reference such as ferrocene. From these potentials, potentials from a saturated calomel electrode may be calculated using well known techniques.

The electrolysis may be conducted in a standard electrolytic cell containing an anode and cathode (also referred to as the working electrode and counter electrode, respectively). Suitable materials of construction for the cell include glass, plastic, ceramic, glass coated metal, etc. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. A third, buffering or spacer, compartment may further separate the working electrode compartment and counter electrode compartment. The working electrode is immersed in a reaction medium comprising the disilane compound, solvent, supporting electrolyte, and any other materials desired for moderating the electrolysis or stabilizing the resulting complex. The counter electrode is immersed in a mixture of the solvent and an electrolyte comprising the $A^-$ anion, which electrolyte may also be the supporting electrolyte. The desired voltage may be determined by theoretical calculations or determined experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, nearly complete conversion of the disilane can be easily detected. Desirably, conversions from 50 to 80 percent of theoretical are utilized to avoid contamination of the desired reaction product with further electrolytic decomposition products.

Suitable supporting electrolytes more preferably include salts corresponding to the formula:

$G^+A^-$;

wherein:

$G^+$ is a cation which is nonreactive towards the starting disilane and resulting complex, and $A^-$ is as previously defined.

Examples of cations, $G^+$, include tetrahydrocarbyl substituted ammonium or phosphonium cations wherein each hydrocarbyl group has up to 10 carbon atoms. Preferred supporting electrolytes are tetraalkylammonium salts of tetrakis(perfluoroaryl) borates, especially tetra-n-butylammonium tetrakis(pentafluorophenyl)borate.

During the electrolysis the cation of the supporting electrolyte passes to the counter electrode and the noncoordinating compatible anion, $A^-$, migrates to the working electrode to become the anion of the resulting oxidized product. Either the solvent or the cation of the supporting electrolyte is reduced at the counter electrode in equal equivalent quantity with the amount of oxidized silylium cation formed at the working electrode. Also, since two moles of silylium complex are formed for each mole of disilane compound employed, the molar amount of disilane compound used is generally approximately one-half the molar quantity of Group 4 metal complex used.

Turning once again to the Group 4 metal containing complexes of the present catalyst system, suitable L groups include any anionic, n-electron containing moiety capable of forming a delocalized bond with the Group 4 metal. Examples include cyclopentadienyl, allyl, and polyenyl groups, as well as substituted derivatives of such groups. Preferred L groups include, cyclopentadienyl, indenyl, fluorenyl, tetrahydroindenyl, tetrahydrofluorenyl, octahydrofluorenyl, pentadienyl, cyclohexadienyl, cyclooctadienyl, dihydronaphthalenyl, hexahydronaphthalenyl, dihydroanthracenyl, hexahydroanthracenyl, decahydroanthracenyl groups, and alkyl substituted derivatives of such groups.

By the term "derivative" when used to describe the above substituted, delocalized n-bonded groups is meant that each atom in the delocalized n-bonded group is substituted (subject to valence limits) with a radical, R' independently each occurrence selected from the group consisting of hydrogen, hydrocarbyl, silyl, germyl, siloxy, hydrocarbyloxy, cyano, halo and combinations thereof, said R' (other than hydrogen, cyano and halo) having up to 20 non-hydrogen atoms. In addition two or more such R' radicals may together form a fused ring system. Examples of the latter are the previously mentioned indenyl-, tetrahydroindenyl-, fluorenyl-, octahydrofluorenyl-, dihydroanthracenyl, hexahydroanthracenyl, and decahydroanthracenyl groups.

Suitable complexes include those containing either one or two L groups. The latter complexes include those containing a bridging group linking the two L groups. Preferred bridging groups are those corresponding to the formula $(ER^*_2)_x$ wherein E is silicon or carbon, $R^*$ independently each occurrence is hydrogen or a group selected from silyl, hydrocarbyl and combinations thereof, said $R^*$ having up to 30 carbon or silicon atoms, and x is 1 to 8. Preferably, $R^*$ independently each occurrence is methyl, benzyl, tertbutyl or phenyl.

Examples of the foregoing bridged bis(L) containing complexes are compounds corresponding to the formula:

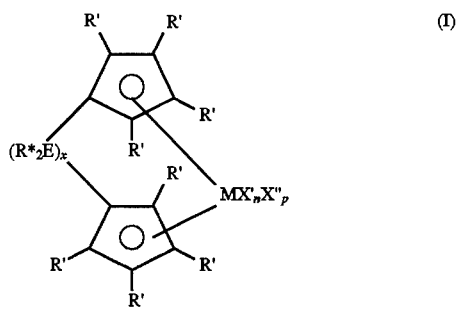

(I)

wherein:

M, E, $R^*$, R', X', X" n and p are as previously defined.

Such bridged structures are especially suited for the preparation of polymers having stereoregular molecular structure. In such capacity it is preferred that the complex possess $C_S$ symmetry or possess a chiral, stereorigid structure. Examples of the first type are compounds possessing different delocalized n-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem*, 232, 233–47, (1982).

Exemplary bridged cyclopentadienyl moieties in the complexes of formula (I) are:
(dimethylsilyl-bis-cyclopentadienyl),
(dimethylsilyl-bis-methylcyclopentadienyl),
(dimethylsilyl-bis-ethylcyclopentadienyl,
(dimethylsilyl-bis-t-butylcyclopentadienyl),
(dimethylsilyl-bis-tetramethylcyclopentadienyl),
(dimethylsilyl-bis-indenyl),
(dimethylsilyl-bis-tetrahydroindenyl),
(dimethylsilyl-bis-fluorenyl),
(dimethylsilyl-bis-tetrahydrofluorenyl),
(dimethylsilyl-cyclopentadienylfluorenyl), (1,1,2,2-tetramethyl-1,2-disilyl-biscyclopentadienyl),
(1,2-bis(cyclopentadienyl)ethane, and
(isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together with M form a metallocyclopentene. Most preferred X" groups are $C_{1-20}$ hydrocarbyl groups.

Suitable divalent X substituents preferably include groups containing up to 30 nonhydrogen atoms comprising at least one atom that is oxygen, sulfur, boron or a member of Group 14 of the Periodic Table of the Elements directly attached to the delocalized n-bonded group, and a different atom, selected from the group consisting of nitrogen, phosphorus, oxygen or sulfur that is covalently bonded to M.

Preferably the Group 4 metal complexes utilized in the present invention correspond to the formula:

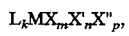

or a dimer thereof wherein:

L is an anionic, delocalized, n-bonded group that is bound to M, containing up to 50 nonhydrogen atoms;

M is a metal of Group 4 of the Periodic Table of the Elements in the +2, +3 or +4 formal oxidation state;

X is a divalent substituent of up to 50 nonhydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M, and further optionally X' and X" may be bonded together thereby forming a moiety that is both covalently bound to M and coordinated thereto by means of Lewis base functionality;

k is 1;

m is 1;

n is a number from 0 to 3;

p is an integer from 1 to 2; and the sum, k+m+p, is equal to the formal oxidation state of M.

Cationic complexes formed upon combination of the above preferred Group 4 metal complexes wherein M is in the +4 formal oxidation state with the silylium compound would therefor correspond to the formula:

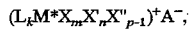

or a dimer thereof wherein:

M* is a metal of Group 4 of the Periodic Table of the Elements in the +4 formal oxidation state;

L, X, X', X", A⁻, k, m, n and p are as previously defined for the above preferred metal complexes.

According to the present invention, highly preferred Group 4 metal complexes for use in formation of the catalyst systems of the invention are those containing one and only one cyclic, delocalized, anionic, n-bonded group, said complexes corresponding to the formula:

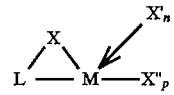

wherein:

M, X, X' and X" are as previously defined. Such complexes are known in the art as constrained geometry complexes.

More highly preferred metal coordination complexes according to the present invention correspond to the formula:

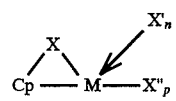

wherein X, M and X" are as previously defined; and

Cp is a $C_5H_4$ group bound to X and bound in an η5 bonding mode to M or is such an η5 bound group substituted with from one to four substituents independently selected from hydrocarbyl, silyl, germyl, halo, cyano, and combinations thereof, said substituent having up to 20 nonhydrogen atoms, or optionally, two or more such substituents (except cyano or halo) together cause Cp to have a fused ring structure.

Most highly preferred Group 4 metal coordination complexes used according to the present invention correspond to the formula:

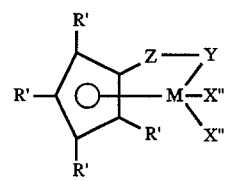

wherein:

M is titanium or zirconium in the +4 formal oxidation state;

R' each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

X" is halo, or a hydrocarbyl, hydrocarbyloxy or silyl group, said group having up to 20 nonhydrogen atoms;

Y is —O—, —S—, —NR*—, —PR*—; and

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*2$;

wherein:

R* each occurrence is independently hydrogen, or a member selected from hydrocarbyl, silyl, halogenated alkyl, halogenated aryl, and combinations thereof, said R* having up to 10 non-hydrogen atoms, and optionally, two R* groups from Z (when R* is not hydrogen), or an R* group from Z and an R* group from Y form a ring system.

Further in such most highly preferred embodiment, R' independently each occurrence is hydrogen, hydrocarbyl, silyl, halo and combinations thereof said R' having up to 10 non-hydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen) are linked together, the entire $C_5R'_4$ group thereby being, for example, an indenyl, tetrahydroindenyl, fluorenyl, tetrahydrofluorenyl, or octahydrofluorenyl group.

Further most highly preferably, at least one of R' or R* is an electron donating moiety. By the term "electron donating" is meant that the moiety is more electron donating than hydrogen. Also most highly preferably, Y is a nitrogen or phosphorus containing group corresponding to the formula —N(R")— or —P(R")—, wherein R" is $C_{1-10}$ hydrocarbyl.

Illustrative Group 4 metal complexes that may be employed in the practice of the present invention include:

complexes having only one L grouping including constrained geometry complexes:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
($\eta^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-$\eta$-1,4,5,6,7,8-hexahydronaphthalenyl)titaniumtrimethyl,
(1,1,2,3-tetramethyl-2,3,4,9,10-$\eta$-1,4,5,6,7,8-hexahydronaphthalenyl)titaniumtrimethyl,
(tert-butylamido)(tetramethyl-$\eta^5$-cyclopentadienyl) dimethylsilanetitanium dichloride,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)1,2-ethanediyltitanium dimethyl,
(tert-butylamido)(tetramethyl-$\eta^5$-indenyl)dimethylsilanetitanium dimethyl,
(tert-butylamido)(tetramethyl-$\eta^5$-cyclopentadienyl) dimethylsilanetitanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (II) s-trans-$\eta^4$-1,4-diphenyl-1,3-butadiene,
dimethylsilanetitanium (IV) s-cis-$\eta^4$-1,4-diphenyl-1,3-butadiene,
(tert-butylamido)(tetramethyl-$\eta^5$-cyclopentadienyl) dimethylsilanetitanium (II) s-trans-$\eta^4$-1,4-dibenzyl-1,3-butadiene,
(tert-butylamido)(tetramethyl-$\eta^5$-cyclopentadienyl) dimethylsilanetitanium (II) s-trans-$\eta^4$-2,4-hexadiene,
(tert-butylamido)(tetramethyl-$\eta^5$-cyclopentadienyl) dimethylsilanetitanium (II) s-trans-$\eta^4$-3-methyl-1,3-pentadiene,
(tert-butylamido)($\eta^5$-2,4-dimethyl-1,3-pentadien-2-yl) dimethylsilanetitanium dimethyl,
(tert-butylamido)(1,1-dimethyl-2,3,4,9,10-$\eta$-1,4,5,6,7,8-hexahydronaphthalen-4-yl) dimethylsilanetitaniumdimethyl, and
(tert-butylamido)(1,1,2,3-tetramethyl-2,3,4,9,10-$\eta$-1,4,5,6,7,8-hexahydronaphthalen-4-yl) dimethylsilanetitaniumdimethyl.

bis(L) containing complexes including bridged complexes:
biscyclopentadienyltitaniumdimethyl,
biscyclopentadienyltitaniumdiethyl,
cyclopentadienyltitaniumdiisopropyl,
biscyclopentadienyltitaniumdiphenyl,
cyclopentadienyltitaniumdibenzyl,
biscyclopentadienyltitanium-2,4-pentadienyl,
biscyclopentadienyltitaniummethylmethoxide,
biscyclopentadienyltitaniummethylchloride,
bispentamethylcyclopentadienyltitaniumdimethyl,
bisindenyltitaniumdimethyl,
indenylfluorenyltitaniumdiethyl,
bisindenyltitanium methyl 2-(dimethylamino)benzyl,
bisindenyltitanium methyl fluoride,
bistetrahydroindenyltitanium methyl trimethylsilyl,
bispentamethylcyclopentadienyltitaniumdiisopropyl,
bispentamethylcyclopentadienyltitaniumdibenzyl,
bispentamethylcyclopentadienyltitaniummethylmethoxide,
bispentamethylcyclopentadienyltitaniummethylchloride,
(dimethylsilyl-bis-cyclopentadienyl)titaniumdimethyl,
(dimethylsilyl-bis-pentamethylcyclopentadienyl)titanium-2,4-pentadienyl,
(dimethylsilyl-bis-t-butylcyclopentadienyl) titaniumdichloride,
(methylene-bis-pentaamethylcyclopentadienyl)titanium (III) 2-(dimethylamino)benzyl,
(dimethylsilyl-bis-indenyl)titaniumdichloride,
(dimethylsilyl-bis-tetrahydroindenyl)s-trans-$\eta^4$-1,4-diphenyl-1,3-butadiene,
(dimethylsilyl-bis-fluorenyl)titaniumdichloride,
(dimethylsilyl-bis-tetrahydrofluorenyl)titaniumdi (trimethylsilyl),
(dimethylsilyl-pentamethylcyclopentadienylfluorenyl) titaniumdimethyl, and
(isopropylidene-cyclopentadienyl-fluorenyl) titaniumdibenzyl.

Other compounds which are useful in the preparation of catalyst compositions according to this invention, especially compounds containing other Group 4 metals, will, of course, be apparent to those skilled in the art.

In the most preferred embodiment —Z—Y— is an amidosilyl or amidoalkyl group of up to 10 nonhydrogen atoms, especially a (t-butylamido)(dimethylsilyl) or 1-(t-butylamido)-2-ethyl group.

The chemical reactions which occur in forming the catalysts of this invention, when a preferred, boron containing compound is used as the second component, are believed to be as follows:

$$L_kMX'_mX''_nX''_p + (R_3Si)^+(BQ_4)^- \rightarrow (L_kMX'_mX''_nX''_{p-1}(X')_q))^+(BQ_4)^- + (R_3Si)X''$$

where in L, M, X', X", X, R, k, m, n, p and q have the previously identified meanings, and Q is a bulky, inert, anionic ligand group of the borate anion, especially pentafluorophenyl.

In general, the stability of the silane causes the reaction to be driven to completion thereby resulting in increased yields of the desired cationic catalyst. Accordingly the resulting catalysts are extremely active and effective polymerization catalysts.

In general, the catalyst can be prepared by combining the two components (the Group 4 metal complex and silylium compound) in a suitable solvent at a temperature within the range from about −100° C. to about 300° C. The catalyst may be separately prepared prior to use by combining the respective components or prepared in situ by combination in the presence of the monomers to be polymerized. It is preferred to form the catalyst in situ due to the exceptionally high catalytic effectiveness of catalysts prepared in this manner. While the catalysts may not contain pyrophoric species, the catalysts' components are sensitive to both moisture and oxygen and should be handled and transferred in an inert atmosphere such as nitrogen, argon or helium. Additional components may be incorporated into the catalyst system if desired. Suitable additional components include alumoxanes, especially methylalumoxane and triisopropylaluminum modified methylalumoxane, Lewis acids such as trialkylaluminum compounds containing from 1 to 6 carbons in each alkyl group, and Lewis bases, such as $C_{1-4}$ dialkyl ethers and tetrahydrofuran.

The catalysts may be used to polymerize ethylenically unsaturated monomers having from 2 to 100,000 carbon atoms either alone or in combination. Certain of the catalysts may be used to form tactic polymers, especially isotactic polypropylene, syndiotactic polypropylene and syndiotactic polystyrene, as is previously known in the art utilizing previously known activating cocatalysts in place of the silylium compounds used in the present invention. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain, macromolecular α-olefins, and mixtures thereof. Other preferred monomers include styrene, $C_{1-4}$ alkyl substituted styrene, tetrafluoroethylene, vinylbenzocyclobutane, ethylidenenorbornene, allylbenzene, 1,4-hexadiene, 1,7-octadiene, vinylcyclohexane, 4-vinylcyclohexene, divinylbenzene, and mixtures thereof with ethylene.

In general, the polymerization may be accomplished at conditions well known in the prior art for Ziegler-Natta or Kaminsky-Sinn type polymerization reactions, i.e., temperatures from 0°–250° C. and pressures from atmospheric to 10,000 atmospheres (0.1 to 1000 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for polymerization are noncoordinating, inert liquids. Examples include straight and branched-chain hydrocarbons such as isobutane, butane, pentane, hexane, heptane, octane, isopentane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkylsubstituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1,7-octadiene, 1-octene, 1-decene, styrene, divinylbenzene, ethylidenenorbornene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, now abandoned as well as U.S. Ser. No. 08/10958, filed Jan. 29, 1993, now abandoned the teachings or which are hereby incorporated by reference herein.

One such polymerization process comprises:

contacting, optionally in a solvent, one or more α-olefins with a catalyst according to the present invention, in one or more continuous stirred tank or tubular reactors, or in the absence of solvent, optionally in a fluidized bed gas phase reactor, connected in series or parallel, and recovering the resulting polymer.

In another process an ethylene/α-olefin interpolymer composition is prepared by:

(A) contacting ethylene and at least one other α-olefin under polymerization conditions in the presence of a catalyst composition of the present invention in at least one reactor to produce a first interpolymer or optionally a solution of a first interpolymer, (B) contacting ethylene and at least one other α-olefin under polymerization conditions and at a higher polymerization reaction temperature than used in step (A) in the presence of a heterogeneous Ziegler catalyst in at least one other reactor to produce a second interpolymer optionally in solution, and (C) combining the first interpolymer and second interpolymer to form an ethylene/α-olefin interpolymer blend composition, and (D) recovering the ethylene/α-olefin interpolymer blend composition.

Preferably the heterogeneous Ziegler catalyst comprises:

(i) a solid support component comprising magnesium halide, silica, modified silica, alumina, aluminum phosphate, or a mixture thereof, and (ii) a transition metal component represented by the formula:

$$TrX''_u(X''')_{v-u}, \text{ or } TrX''uO(X''')_{v-u-2},$$

wherein:

Tr is a Group 4, 5, or 6 metal,

O is oxygen,

X" is halogen,

X''' is independently selected from hydrocarbyl, silyl, hydrocarbyloxy or siloxy having up to 10 non-hydrogen atoms, u is a number from 0 to 6 that is less than or equal to v, and v is the formal oxidation number of Tr.

These polymerizations are generally carried out under solution conditions to facilitate the intimate mixing of the two polymer-containing streams. The foregoing technique allows for the preparation of ethylene/α-olefin interpolymer compositions having a broad molecular weight distribution and broad composition distribution. Preferably, the heterogeneous catalyst is also chosen from those catalysts which are capable of efficiently producing the polymers under high temperature, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition of the present invention to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:

(i) a solid support component comprising a magnesium halide or silica, and (ii) a transition metal component represented by the formula:

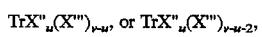

wherein:

Tr, X", X'", u, and v are as previously defined.

The foregoing technique also allows for the preparation of ethylene/α-olefin interpolymer compositions having a broad range of molecular weight distributions and broad composition distributions. Particularly desirable α-olefins for use in the process of the present invention are mixtures of ethylene and $C_{4-8}$ α-olefins, most desirably mixtures of ethylene and 1-octene.

The skilled artisan will appreciate that the invention disclosed herein may be practiced in the absence of any component which has not been specifically disclosed. The following examples are provided as further illustration thereof and are not to be construed as limiting. Unless stated to the contrary all parts and percentages are expressed on a weight basis.

EXAMPLE 1

(Tert-butylamido)dimethyl(tetramethyl-$\eta^5$-cyclopentadienyl)silanetitanium dimethyl and triethylsilylium tetrakispentafluorophenyl borate A. Preparation of (tert-butylamido)dimethyl (tetramethyl-$\eta^5$-cyclopentadienyl) silanetitaniumdimethyl In a drybox, 0.20 g of $TiCl_3(THF)_3$ was suspended in 40 mL of tetrahydrofuran (THF). 0.277 g of solid (tetramethylcyclopentadienyl)(t-butylamino)dimethylsilane diGrignard $(Me_4C_5SiMe_2N-t-BuMg_2Cl_2(THF)_2)$ was added, resulting in a color change from pale blue to deep purple. After stirring for 5 minutes, 0.17 ml of a 1.56M solution of methylenechloride in THF was added. The color changed to bright yellow over a period of one hour. The THF was removed under reduced pressure. The product was recovered by extraction in pentane. The yield of yellow (t-butylamido)dimethyl(tetramethyl-$\eta^5$-cyclopentadienyl) silanetitanium dichloride was 0.144 g, 72.4 percent. The corresponding dimethyl complex is formed by reaction with methyl Grignard.

B. Preparation of triethylsilylium tetrakispentafluorophenyl borate

A flask was charged with triphenylcarbenium tetrakispentafluoropenylborate (400 mg, 0.434 mmol) and 4 mL of triethylsilane. After reaction for 16 hours the resulting slurry was filtered, washed with hexane and the volatile components were removed under reduced pressure to give a white solid. Yield of triethylsilylium tetrakispentafluorophenyl borate was 325 mg, 94.3 percent.

C. Polymerization

A two liter stirred reactor was charged with 741 g of mixed alkane solvent (Isopar-E™ available from Exxon Chemicals Inc.) and 119 g of 1-octene comonomer. Hydrogen (25 Δpsi, Δ170 kPa) was added to the reactor by differential pressure expansion from a 80 mL addition tank. The reactor was heated to 140° C., stirred at 1200 rpm and saturated with ethylene at 3.5 MPa. Catalyst and cocatalyst were mixed in a dry box by pipetting toluene solutions of (N-t-butylamido)dimethyl($\eta^5$-cyclopentadienyl) silanetitanium (IV) dimethyl and trimethylsilylium tetrakispentafluorophenyl borate to provide 1.0 μmol of each compound. The resulting solution was transferred to a catalyst addition tank and injected into the reactor and the addition line washed with toluene which was also injected into the reactor. The polymerization was allowed to proceed with ethylene being added on demand. The maximum temperature rise was 24° C. After 15 minutes the polymer solution was removed from the reactor. A hindered phenol antioxidant (Irganox™ 1010 available from Ciba Geigy Corp.), 100 mg, was added to the resulting ethylene/1-octene copolymer. Volatiles were removed from the polymer solution under reduced pressure in an oven at about 130° C. for approximately 18 hours. The polymer yield was 98.5 g.

EXAMPLE 2

(N-t-butylamido)(dimethyl)(4,4-dimethyl-$\eta^5$-1,3-cyclohexadien-1-yl)silanetitanium (IV) dimethyl and triethylsilylium-diethylether tetrakispentafluorophenylborate A1. Preparation of 5,5-dimethyl-1,3-cyclohexadiene/3,3-dimethyl-1,4-cyclohexadiene isomeric mixture In a glass flask under nitrogen atmosphere, 50.0 g (0.357 mol) 1,1-dimethyl-3,5-diketocyclohexane was slurried in about 500 mL of diethyl ether. After cooling the slurry in an ice bath, 13 g (0.342 mol) of $LiAlH_4$ was slowly added. The reaction mixture was allowed to warm to room temperature and was stirred for 2 hours, after which 14 g (0.369 mol) of additional $LiAlH_4$ was added. The reaction mixture was refluxed for 2 hours, then stirred overnight. Workup occurred as follows: After the reaction mixture was cooled in an ice bath, 27 mL of water was slowly added, followed by 27 mL of 15 weight percent, aqueous NaOH solution, then 81 mL of water. The resulting solids were filtered off and washed with diethyl ether. The combined ether solutions were concentrated by evaporation. To the resulting pale yellow product was added 10 mL of 9M, aqueous $H_2SO_4$. The product was collected after distillation using a short path distillation column up to a pot temperature of 145° C. Additional $H_2SO_4$ was added and a second distillation was performed. After washing with 10 weight percent, aqueous $Na_2CO_3$, then with water, the product was dried with anhydrous $MgSO_4$. The product was fractionally distilled, with fractions boiling up to about 100° C. being collected. The yield was 12 g. of the isomeric mixture depicted as follows:

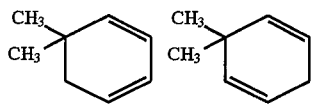

A2. Preparation of potassium 6,6-dimethyl-cyclohexadienide

To 14.0 g(0.111 mol) of potassium t-amylate (KOC$(CH_3)_2C_2H_5$) in 200 mL of pentane was added 44.4 mL of 2.5M (0.111 mol) butyl lithium in hexane with formation of a small amount of brownish insoluble material. To this was added 12.0 (0.111 mol) of the previously formed dimethyl-cyclohexadiene isomeric mixture. A bright orange product resulted. After stirring overnight, the color became brownish orange. The product was filtered, washed several times with pentane, then dried under reduced pressure. The yield of orange powder was 11.8 g, 72.7 percent.

A3. Preparation of (N-t-butylamino)(dimethyl)(4,4-dimethylcyclohexadien-1-yl)silane isomeric mixture To a solution of 5.46 g (32.9 mmol) $ClSi(CH_3)_2NC(CH_3)_3$ (obtained according to the technique of EP-A-563,365) in tetrahydrofuran (THF) was slowly added 4.50 g (30.8 mmol) of solid potassium dimethylcyclohexadienide isomeric mixture. After stirring overnight, the reaction mixture was filtered and the solvent was removed under reduced pressure. The residue was extracted with pentane, the resulting slurry was filtered and the solvent was removed from the filtrate. Purification by Kugelrohr distillation gave 3.58 g of product,49.0 percent yield. $^1$HNMR($C_6D_6$)Δ 5.69 (d, 10.2 Hz, 2H), 5.45 (d, 9.9 Hz, 2H), 2.30 (s, 1H), 1.13 (s, 3H), 1.12(s, 3H), 1.07 (s, 9H), 0.12 (s, 6H). The structures of the isomeric products are depicted as follows:

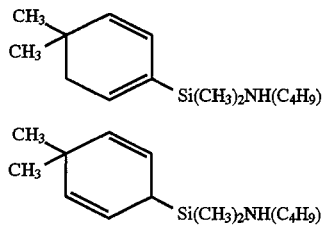

A4. Preparation of dilithium(N-t-butylamido)(dimethyl)-(4,4-dimethylcyclohexadienyl)silane isomeric mixture To 3.58 g (15.1 mmol) of (N-t-butylamino)(dimethyl)(dimethylcyclohexadienyl)silane in 75 mL of diethyl ether was added 12.6 mL of 2.52M n-butyl lithium in hexane. There suiting yellow reaction solution was stirred for several days, during which time a large amount of precipitate had formed. The reaction mixture was refluxed for several hours, then it was filtered. The solid was washed with hexane and then dried under reduced pressure. The yield of the pale yellow powder was 2.01 g, 53.5 percent yield.

A5. Preparation of (N-t-butylamido)(dimethyl)(6,6-dimethyl-$\eta^5$-cyclohexadien-3-yl)silanetitanium (IV) dichloride Dilithium(N-t-butylamido)(dimethyl)(4,4-dimethyl-$\eta^5$-cyclohexadienyl)silane(1.50 g,6.01 mmol) was added by means of a constant addition funnel over a 5 minute period at 25° C. to a 250 ml glass flask containing 2.23 g (6.01 mmol) of $TiCl_3$•$(THF)_3$ and 125 mL of THF. A dark brown mixture formed immediately. To this reaction mixture $PbCl_2$ (1.80 g, 6.48 mmol) was added as a solid at 25 ° C. and the resulting mixture stirred for 2 hours. The volatiles were removed under reduced pressure and the solid triturated once with hexane. Hexane (50 mL) was then added and the mixture filtered through Celite™ diatomaceous earth filter aid, to give a dark brown solution. Concentration of the solution to 30 mL, cooling to −78° C., and filtration gave brown crystals of the desired product. Yield was 1.01 g,47 percent. The structure of the resulting product is as follows:

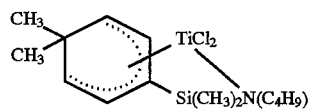

A6. Preparation of(N-t-butylamido)(dimethyl)(4,4-dimethyl-$\eta^5$-1,3-cyclohexadien-1-yl)silanetitanium (IV) dimethyl 0.049 g Of (N-t-butylamido)(dimethyl)(4,4-dimethyl-$\eta^5$-cyclohexadien-1-yl)silanetitanium dichloride (0.12 mmol) was dissolved in 10 ml of diethyl ether. To this solution 0.08 ml of magnesium methyl iodide ($CH_3MgI$)(3.0M in THF) was added dropwise at 25° C. with stirring over a 20 min period. Upon completion of the addition of the $CH_3MgI$ the solution was stirred for 20 minutes. After this time period the diethyl ether was removed under reduced pressure and the residue extracted with pentane. The solution was then filtered, the filtrate was evaporated to dryness under reduced pressure to give 0.026 g (66 percent yield) of the desired product. 1H NMR ($C_6D_6$): d5.25 (d, 2H), 5.05 (d, 2H), 1.46 (s, 9H), 1.32 (s 6H), 1.18 (s, 3H), 0.66 (s, 3H), 0.20 (s, 6H).

B. Triethylsilylium Tetrakispentafluorophenylborate

The silylium borate salt was prepared according to Example 1, part B.

C. Polymerization

A two liter stirred reactor was charged with 744 g of mixed alkane solvent (Isopar-E™ available from Exxon Chemicals Inc.) and 126 g of 1-octene comonomer. Hydrogen (25 Δpsi, Δ170 kPa) was added to the reactor by differential pressure expansion from a 80 mL addition tank. The reactor was heated to 140° C., stirred at 1200 rpm and saturated with ethylene at 3.5 MPa (500 psi). Catalyst and cocatalyst were mixed in a dry box by pipetting toluene solutions of (N-t-butylamido)(dimethyl)(4,4-dimethyl-$\eta^5$-1,3-cyclohexadien-1-yl)silanetitanium (IV) dimethyl and triethylsilylium tetrakispentafluorophenyl borate to provide 2.0 μmol of each compound. The resulting solution was transferred to a catalyst addition tank and injected into the reactor and the addition line washed with toluene and also injected into the reactor. The polymerization was allowed to proceed with ethylene being added on demand. After 15 minutes the polymer solution was removed from the reactor. Volatiles were removed from the ethylene/1-octene copolymer solution under reduced pressure in an oven at about 130° C. for approximately 18 hours. The yield was 8.2 g.

EXAMPLE 3

(Tert-butylamido)dimethyl(tetramethyl-$\eta^5$-cyclopentadienyl)silanetitanium dimethyl and trimethylsilylium•diethylether tetrakis(pentafluorophenyl)borate

A. (Tert-butylamido)dimethyl(tetramethyl-$\eta^5$-cyclopentadienyl)silanetitanium dimethyl The titanium complex was prepared according to Example 1, part A.

B. Trimethymethylsilium Tetrakis(pentafluorophenyl)borate•$(OC_2H_5)_2$

A flask was charged with 1.00 g of LiB($C_6F_5$)$_4$•2.5 Et$_2$O (1.00 g, 1.15 mmol) and 40 mL of trimethylsilyl chloride. The contents were stirred overnight to give a cloudy solution which was filtered through Celite™ brand diatomaceous earth filter aid to give a clear colorless solution. The volatiles were removed in vacuo to give a white slightly oily solid. Trituration and stirring with hexane gave a white solid which was isolated by filtration. Drying under reduced pressure yielded the silylium salt as a white powder (0.60 g, 63 percent).

C1. Polymerization

A two liter stirred reactor was charged with 520 g of toluene and 147 g of 1-octene comonomer. The reactor was heated to 80° C., stirred at 1200 rpm and saturated with ethylene at 450 kPa (65 psi). Catalyst and cocatalyst were mixed in a dry box by pipetting toluene solutions of (N-t-butylamido)dimethyl-(tetramethyl-$\eta^5$-cyclopentadienyl)silanetitanium (IV) dimethyl and trimethylsilylium tetrakis(pentafluorophenyl)borate•$(OC_2H_5)_2$ to provide 1.0 μmol of each compound. The resulting yellow solution was transferred to a catalyst addition tank and injected into the reactor and the addition line washed with toluene which was injected into the reactor. The polymerization was allowed to proceed with ethylene being added on demand. Total exotherm was 5.6 ° C. After 10 minutes the polymer solution was removed from the reactor. Volatiles were removed from the ethylene/1-octene copolymer solution under reduced pressure in an oven at about 130 ° C. for approximately 18 hours. The yield was 24.0 g.

C2. Polymerization

A two liter stirred reactor was charged with 718 g of Isopar-E™ solvent and 110 g of 1-octene comonomer. Hydrogen (36 Δpsi, Δ250 kPa) was added to the reactor by differential pressure expansion from a 80 mL addition tank. The reactor was heated to 140° C., stirred at 1200 rpm and saturated with ethylene at 3.5 MPa (500 psi). Catalyst and cocatalyst were mixed in a dry box by pipetting toluene solutions of (N-t-butylamido)dimethyl(tetramethyl-$\eta^5$-cyclopentadienyl)silanetitanium (IV) dimethyl and trimethylsilylium tetrakis(pentafluorophenyl)borate•$(OC_2H_5)_2$ to provide 1.0 μmol of each compound. The resulting solution was transferred to a catalyst addition tank and injected into the reactor and the addition line washed with toluene and also injected into the reactor. The polymerization was allowed to proceed with ethylene being added on demand. Total exotherm was again 5.6° C. After 15 minutes the polymer solution was removed from the reactor. Volatiles were removed from the ethylene/1-octene copolymer solution under reduced pressure in an oven at about 130° C. for approximately 18 hours. The yield of ethylene/1-octene copolymer was 38.4 g.

EXAMPLE 4

(Tert-butylamido)dimethyl(tetramethyl-$\eta^5$-cyclopentadienyl)silanetitanium dimethyl and trimethylsilylium tetrakis(pentafluorophenyl)borate

A. (Tert-butylamido)dimethyl(tetramethyl-$\eta^5$-cyclopentadienyl)silanetitanium dimethyl The titanium complex was prepared according to Example 1, part A.

B. Electrochemical Generation of Trimethylsilylium Tetrakispentafluorophenylborate A standard H-cell for electrolysis comprising two electrode wells separated by a fine glass frit, platinum mesh working and counter electrodes, and a silver wire reference electrode was placed inside an inert atmosphere glove box filled with argon. Each half of the cell was filled with 1,2-difluorobenzene solvent (5 ml in the working compartment, 4 ml in the counter compartment) and tetra(n-butylammonium) tetrakis(pentafluorophenyl)borate supporting electrolyte (15 mmole in each compartment). Hexamethyldisilane was added to the working compartment (10 mmole). The solution was stirred and the potential stepped to the appropriate value to start oxidation of the Si—Si bond, +2.4 V versus a saturated calomel electrode. The reaction was stopped when 10 mmole of $(CH_3)_3Si^+$ were produced. The working compartment solution was then pipetted into a round bottom flask and the solvent was removed under vacuum. The product was dissolved in toluene to form a 0.005M solution used as cocatalyst for the polymerization.

C. Polymerization

A two liter stirred reactor was charged with 714 g of mixed alkane solvent (Isopar-E™ available from Exxon Chemicals Inc.) and 107 g of 1-octene comonomer. Hydrogen (32 Δpsi, Δ220 kPa) was added to the reactor by differential pressure expansion from a 80 mL addition tank. The reactor was heated to 140° C., stirred at 1200 rpm and saturated with ethylene at 3.5 MPa. Catalyst and cocatalyst were mixed in a dry box by pipetting toluene solutions of (N-t-butylamido)dimethyl($\eta^5$-cyclopentadienyl)silanetitanium (IV) dimethyl and trimethylsilylium tetrakispentafluorophenyl borate prepared by electrolysis to provide 1.0 μmol of each compound. The resulting solution was transferred to a catalyst addition tank and injected into the reactor and the addition line washed with toluene which was also injected into the reactor. The polymerization was allowed to proceed with ethylene being added on demand. After 15 minutes the polymer solution was removed from the reactor. A hindered phenol antioxidant (Irganox™ 1010 available from Ciba Geigy Corp.), 100 mg, was added to the resulting ethylene/1-octene copolymer. Volatiles were removed from the polymer solution under reduced pressure in an oven at about 130° C. for approximately 18 hours. The yield of ethylene/1-octene copolymer was 99.1 g.

What is claimed is:

1. A process for preparing a silylium salt corresponding to the formula:

$$R_3Si(X')_q{}^+A^-$$

wherein

R independently each occurrence is selected from the group consisting of hydrocarbyl, silyl, hydrocarbyloxy, dihydrocarbylamino, and combinations thereof having up to 20 nonhydrogen atoms, X' is a neutral Lewis base having up to 20 non-hydrogen atoms; q is zero or one; and $A^-$ is a noncoordinating, compatible anion, said process comprising oxidizing by electrolyzing a solution comprising a disilane compound corresponding to the formula:

$$R_3SiSiR_3$$

wherein R is as previously defined, in the presence of a source of the noncoordinating counter ion, $A^-$ and optionally a neutral Lewis base.

2. A process according to claim 1 wherein the oxidation is an electrolysis conducted at a potential of at least +0.5 volts versus a saturated calomel electrode.

3. A process according to claim 2 wherein the electrolysis is conducted until conversion of disilane compound is from 50 to 80 percent of theoretical.

* * * * *

UNITED STATES PATENT AND TRADEMARK OFFICE
CERTIFICATE OF CORRECTION

PATENT NO. : 5,625,087

DATED : April 29, 1997

INVENTOR(S) : David D. Devore; Robert E. LaPointe; Robert D. Mussell; David R. Neithamer It is certified that error appears in the above-identified patent and that said Letters Patent is hereby corrected as shown below:

On the cover page, [75], following Inventors: delete "David D. Devore"

Signed and Sealed this

Sixteenth Day of December, 1997

Attest:

BRUCE LEHMAN

Attesting Officer

Commissioner of Patents and Trademarks